United States Patent [19]

Tessier et al.

[11] Patent Number: 4,777,180
[45] Date of Patent: Oct. 11, 1988

[54] PESTICIDAL CYCLOPROPANECARBOXYLATES

[75] Inventors: Jean Tessier, Vincennes; Pierre Girault, Paris, both of France

[73] Assignee: Roussel Uclaf, Paris, France

[21] Appl. No.: 106,143

[22] Filed: Oct. 7, 1987

Related U.S. Application Data

[63] Continuation of Ser. No. 479,199, Mar. 28, 1983, abandoned.

[30] Foreign Application Priority Data

Apr. 8, 1982 [FR] France .................. 82 06162

[51] Int. Cl.$^4$ .................. A01N 43/50; C07D 233/72
[52] U.S. Cl. .................. 514/389; 514/218; 514/269; 540/492; 544/314; 548/312
[58] Field of Search ............ 548/312; 514/389, 218, 514/269; 544/314; 540/492

[56] References Cited

U.S. PATENT DOCUMENTS 4,176,189 11/1979 Itaya et al. .................. 548/312 X Primary Examiner—Richard A. Schwartz
Attorney, Agent, or Firm—Bierman & Muserlian

[57] ABSTRACT

Novel esters in all stereoisomeric forms and mixtures of said isomers of the formula

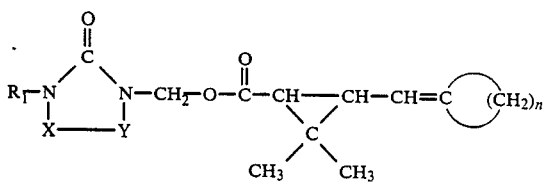

wherein one of X and Y is

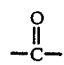

and the other is selected from the group consisting of —$CH_2$—, —$CH_2$—$CH_2$— and —$CH_2$—$CH_2$—$CH_2$—, n is an integer from 2 to 3 and $R_1$ is selected from the group consisting of alkyl of 1 to 3 carbon atoms and alkenyl and alkynyl of 2 to 3 carbon atoms having pesticidal activity.

28 Claims, No Drawings

PESTICIDAL CYCLOPROPANECARBOXYLATES

This is a continuation, of Ser. No. 479,199 filed Mar. 28, 1983, now abandoned

STATE OF THE ART

U.S. Pat. No. 4,176,189 and Pest. Sci., No. 10 (1979), p. 291–294 describe the compound of the formula $$\text{HC}\equiv\text{C}-\text{CH}_2-\text{N}\underset{\underset{\text{C}=\text{O}}{|}}{\overset{\overset{\text{O}}{\parallel}}{\overset{\text{C}}{\diagup\diagdown}}}\text{N}-\text{CH}_2-\text{O}-\overset{\overset{\text{O}}{\parallel}}{\text{C}}-\text{CH}\underset{\underset{\text{CH}_3}{\diagdown\diagup}\text{C}\underset{\text{CH}_3}{\diagup\diagdown}}{\underline{\quad\quad\quad}}\text{CH}-\text{CH}=\text{C}\underset{\diagdown\text{CH}_2-\text{CH}_2}{\diagup\text{CH}_2-\text{CH}_2}$$

which would be a compound of formula I if n were 4. However, the compounds of formula I have a superior pesticidal activity as evidenced by their superior knockdown activity of flies, mosquitoes and other domestic insects.

OBJECTS OF THE INVENTION

It is an object of the invention to provide the novel compounds of formula I and a process for their preparation.

It is another object of the invention to provide novel pesticidal compositions and to provide a novel method of killing pests, especially insects.

These and other objects and advantages of the invention will become obvious from the following detailed description.

THE INVENTION

The novel compounds of the invention are esters in all stereoisomeric forms and mixtures of said isomers of the formula $$\text{R}_1-\text{N}\underset{\text{X}\underline{\quad\quad}\text{Y}}{\overset{\overset{\text{O}}{\parallel}}{\overset{\text{C}}{\diagup\diagdown}}}\text{N}-\text{CH}_2-\text{O}-\overset{\overset{\text{O}}{\parallel}}{\text{C}}-\text{CH}\underset{\underset{\text{CH}_3}{\diagdown\diagup}\text{C}\underset{\text{CH}_3}{\diagup\diagdown}}{\underline{\quad\quad\quad}}\text{CH}-\text{CH}=\text{C}\diagdown(\text{CH}_2)_n \qquad \text{I}$$

wherein one of X and Y is $$-\overset{\overset{\text{O}}{\parallel}}{\text{C}}-$$

and the other is selected from the group consisting of —CH$_2$—, —CH$_2$—CH$_2$— and —CH$_2$—CH$_2$—CH$_2$—, n is an integer from 2 to 3 and R$_1$ is selected from the group consisting of alkyl of 1 to 3 carbon atoms and alkenyl and alkynyl of 2 to 3 carbon atoms.

Among the preferred compound of formula I are those wherein Y is $$-\overset{\overset{\text{O}}{\parallel}}{\text{C}}-$$

and X is methylene and R$_1$ is alkyl of 1 to 3 carbon atoms or alkenyl and alkynyl of 2 to 3 carbon atoms and those wherein X is —CH$_2$— and Y is $$-\overset{\overset{\text{O}}{\parallel}}{\text{C}}-$$

and R$_1$ is alkynyl of 2 to 3 carbon atoms, especially —CH$_2$—C≡CH.

Specific preferred compounds of formula I are the (1-propargyl-2,4-dioxo-imidazolidin-3-yl)-methyl esters of (1R,cis)2,2-dimethyl-3-cyclobutylidenemethyl-cyclopropane-1-carboxylic acid, (1R,trans)2,2-dimethyl-3-cyclobutylidenemethyl-cyclopropane-1-carboxylic acid, (1R,cis)2,2-dimethyl-3-cyclopropylidenemethyl-cyclopropane-1-carboxylic acid and (1R,trans)2,2-dimethyl-3-cyclopropylidenemethyl-cyclopropane-1-carboxylic acid.

The compounds of the invention exist in various stereo isomeric forms due to the existence of asymetric carbon atoms at the 1- and 3-positions of the cyclopropane ring in the acid moiety. The diverse stereoisomeric forms have the configurations (1S,3S), (1R,3R), (1S,3R) and (1R,3S) and racemic mixtures thereof.

The novel process of the invention for the preparation of the compounds of formula I comprises reacting in an organic solvent an alcohol of the formula $$\text{R}_1-\text{N}\underset{\text{X}\underline{\quad\quad}\text{Y}}{\overset{\overset{\text{O}}{\parallel}}{\overset{\text{C}}{\diagup\diagdown}}}\text{N}-\text{CH}_2\text{OH} \qquad \text{II}$$

wherein X, Y and R$_1$ have the above definition or a functional derivative thereof with an acid of the formula $$\text{HO}\overset{\overset{\text{O}}{\parallel}}{\text{C}}-\text{CH}\underset{\underset{\text{CH}_3}{\diagdown\diagup}\text{C}\underset{\text{CH}_3}{\diagup\diagdown}}{\underline{\quad\quad\quad}}\text{CH}-\text{CH}=\text{C}\diagdown(\text{CH}_2)_n \qquad \text{III}$$

wherein n has the above definition or a functional derivative thereof.

Examples of the organic solvent are aliphatic hydrocarbons, aromatic hydrocarbons, ether, tetrahydrofuran, acetonitrile and methylene chloride. The process is preferably effected in the presence of dicyclohexylcarbodiimide and 4-dimethylamino-pyridine.

The alcohols of formula II are known and the process is preferably effected with an alcohol wherein X is —CH$_2$—, Y is

and $R_1$ is —$CH_2$—C≡CH.

The pesticidal compositions of the invention are comprised of a pesticidally effective amount of at least one compound of formula I and an inert carrier. The compositions are useful to combat vegetable parasites, parasites in premises and parasites of warm-blooded animals as well as being useful against insects, nematodes and vegetable and animal acarien parasites.

The compositions of the invention have an especially remarkable knockdown effect against domestic insects such as houseflies, mosquitoes and cockroaches. They are especially useful to combat insects in the agricultural field such as aphides, lepidoptera larvae and coleoptera larvae and they are usually used at a dose of 10 to 300 g of active ingredient per hectare.

The compositions are equally useful to combat vegetable parasites, parasites in premises and warm-blooded animal parasites but are preferably useful as insecticides.

Among the preferred compositions of the invention are those where the active ingredient is selected from the group consisting of (1-propargyl-2,4-dioxo-imidazolidin-3-yl)-methyl esters of (1R,cis)2,2-dimethyl-3-cyclobutylidenemethyl-cyclopropane-1-carboxylic acid, (1R,trans)2,2-dimethyl-3-cyclobutylidenemethyl-cyclopropane-1-carboxylic acid, (1R,cis)2,2-dimethyl-3-cyclopropylidenemethyl-cyclopropane-1-carboxylic acid and (1R,trans)2,2-dimethyl-3-cyclopropylidenemethyl-cyclopropane-1-carboxylic acid.

The compositions destined for agrochemical and premises usage may contain more than one active agent and may also contain other pesticides. The said compositions may be in the form of powders, granules, suspensions, emulsions, solutions, aerosol solutions, combustible strips, baits or other classical preparations used for compositions of this nature.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of formula I.

In an advantageous operation for premises use, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 95% by weight.

In the case of a serpentine insecticide, the inert support may be made, for example, of pyrethrum marc, Tabu powder (or Machilus Thumbergii leaf powder), powder of pyrethrum stems, cedar needle powder, sawdust such as pine sawdust, starch and powder of coconut shells. The active dose in this case is preferably 0.03 to 1% by weight.

The compositions of the invention for use in premises may be prepared as a spraying oil containing the active ingredient and the oil may soak the wick of the lamp which is then subjected to combustion. The concentration of the compound of formula I in the oil is preferably 0.03 to 95% by weight.

The insecticidal compositions as well as the acaricidal and nematocidal compositions of the invention may also contain one or more other pesticides and are in the usual powder, granule, suspension, emulsion or solution form. For acaricide use, the compositions are preferably wettable powders for foliar spraying containing 1 to 80% by weight of the active ingredient or liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

To increase the biological activity of the compositions of the invention, classical synergists may be incorporated therein such as 1-(2,5,8-trioxadodecyl)-2-propyl-4,5-methylenedioxy-benzene(piperonyl butoxide) or N-(2-ethylheptyl)-bicyclo-[2,2,1]-5-heptene-2,3-dicarboximide or piperonyl-bis-2-(2'-n-butoxy-ethoxy)-ethyl acetal (tropital).

The pesticidal compositions of the invention are also useful for combatting animal parasites such as ticks and especially ticks of the Boophilus species, of the Hyalomnia species, of the Amblyomnia species and of the Rhipicephalus species and for combatting all sorts of scabies, especially sarcoptic scabies, psoroptic and chorioptic scabies.

The compositions of the invention show an excellent general tolerance and are equally useful for treating affections created by ticks, lice and scabies.

The said compositions may be administered externally by vaporization, by shampoo, by painting or by bathing. For veterinary usage, the compositions may also be administered by painting the dorsal spine by the "pour on" method as well as being administered digestively or parenterally.

When the compositions are to be used to combat animal parasitic acariens, the active compounds of formula I are very often incorporated into alimentary compositions in association with a nutritive mixture adapted to the animal to be fed. The nutritive mixture will vary depending upon the specific animal but usually contains cereals, sugars and grains, soybean press cake, peanuts and turnsole, meal of animal origin such as fish meal, synthetic amino acids, mineral salts, vitamins and antioxidants.

Another feature of the invention are insecticidal acaricidal or nematocidal compositions containing as an active ingredient at least one compound of formula I and as a second active ingredient at least one pyrethrinoid ester selected from the group consisting of esters of allethrolones, of 3,4,5,6-tetrahydrophthalimido-methyl alcohol, of 5-benzyl-3-furyl-methyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl-cyclopropane-1-carboxylic acids, esters of α-cyano-3-phenoxybenzyl alcohols with 2,2-dimethyl-3-(2,2-dibromovinyl)-cyclopropane-1-carboxylic acids, esters of 3-phenoxy-benzyl alcohol with 2-p-chlorophenyl-2-isopropyl-acetic acids, esters of allethrolones, 3,4,5,6-tetrahydrophthalimido-methyl alcohol, 5-benzyl-3-furyl-methyl alcohol, 3-phenoxy-benxyl alcohol or α-cyano-3-phenoxy-benzyl alcohols with 2,2-dimethyl-3-(1,2,2,2-tetrahaloethyl)-cyclopropane-1-carboxylic
acids where halo is fluorine, chlorine or bromine wherein the compounds of formula I and the above pyrethrinoid esters are in all possible stereoisomer forms.

The latter associated compositions of the invention are of particular interest for combatting by the polyvalence of their action a larger range of parasites or by manifesting a synergistic action in some cases.

The novel method of the invention for combatting parasites such as insects, nematodes and acariens comprises contacting the parasites with a pesticidally effective amount of at least one compound of formula I.

In the following examples there are described several preferred embodiments to illustrate the invention. However, it is to be understood that the invention is not intended to be limited to the specific embodiments.

EXAMPLE 1

(1-propargyl-2,4-dioxo-imidazolidin-3-yl)-methyl(1R,-trans)2,2-dimethyl-3-(cyclobutylidenemethyl)-cyclopropane-1-carboxylate A solution of 3.6 g of (1-propargyl-2,4-dioxo-imidazolidin-3-yl)-methanol in 10 ml of methylene chloride was added at 20° C. to a mixture of 4 g of (1R,trans)2,2-dimethyl-3-(cyclobutylidenemethyl)-cyclopropane-1-carboxylic acid, 4.6 g of dicyclohexyl-carbodiimide, 20 ml of methylene chloride and a catalytic amount of 4-dimethylamino-pyridine and the mixture was stirred at 20° C. for 17 hours and was vacuum filtered. The filtrate was evaporated to dryness under reduced pressure and the residue was chromatographed over silica gel. Elution with a 7-3 cyclohexane-ethyl actate mixture and then a 95-5 benzene-ethyl acetate mixture yielded 1.2 g of (1-propargyl-2,4-dioxo-imidazolidin-3-yl)-methyl(1R,trans)2,2-dimethyl-3-(cyclobutylidenemethyl)-cyclopropane-1-carboxylate.
NMR Spectrum (deuterochloroform):

Peaks at 1.13–1.25 ppm (hydrogens of geminal methyls); at 1.37–1.46 ppm (1-hydrogen of cyclopropyl); at 2.34–2.38–2.42 ppm (acetylenic hydrogen); at 2.5 to 2.9 ppm (hydrogens of 2- and 4-methylenes of cyclobutyl); at 4.1 ppm (5-hydrogens of imidazolidinyl ring); at 4.27–4.32 ppm (hydrogens of propargyl methylene); at 4.7–4.9 ppm (ethylenic hydrogen); at 5.4–5.5 and 5.5–5.7 ppm (hydrogens of methylene α to

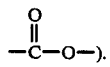

EXAMPLE 2

(1-propargyl-2,4-dioxo-imidazolidin-3-yl)-methyl(1R-,cis)2,2-dimethyl-3-cyclobutylidenemethyl-cyclopropane-1-carboxylate Using the procedure of Example 1, (1R,cis)2,2-dimethyl-3-cyclobutylidenemethyl-cyclopropane-1-carboxylic acid was reacted to obtain (1-propargyl-2,4-dioxo-imidazolidin-3-yl)-methyl(1R,cis)2,2-dimethyl-3-cyclobutylidenemethyl-cyclopropane-1-carboxylate.
NMR Spectrum (deuterochloroform):

Peaks at 1.17–1.25 ppm (hydrogens of geminal methyls); 1.5 to 2.2 ppm (1- and 3-hydrogens of cyclopropyl); at 2.34–2.38–2.42 ppm (acetylenic hydrogen); at 4.3 ppm (hydrogens of propargyl methylene); at 4.1 ppm (5-hydrogens of imidazolidinyl); at 5.5 ppm (hydrogens of methylene α to

at 5.3–5.5 ppm (ethylenic hydrogens). The cyclobutyl hydrogens are marked at 1.5 to 3.0 ppm.

EXAMPLE 3

Using the procedure of Example 1, (1R,cis)2,2-dimethyl-3-cyclopropylidenemethyl-cyclopropane-1-carboxylic acid was reacted to obtain (1-propargyl-2,4-dioxo-imidazolidin-3-yl)methyl(1R,cis)2,2-dimethyl-3-cyclopropylidenemethyl-cyclopropane-1-carboxylate.
NMR Spectrum (deuterochloroform):

Peaks at 1.20–1.32 ppm (hydrogens of geminal methyls); at 1.07–1.10 ppm (hydrogens of methylene of cyclopropylidene); at 1.61–1.75 ppm (1-hydrogen of cyclopropane); at 1.96–2.10–2.24 ppm (3-hydrogen of cyclopropane); at 2.34–2.38–2.42 ppm (acetylenic hydrogen); at 4.3 ppm (hydrogens of propargyl methylene); at 4.1 ppm (5-hydrogens of imidazolidinyl ring); at 5.5 ppm (hydrogens of —CH₂— α to

at 6.0–6.1 ppm (ethylenic hydrogen).

EXAMPLE 4

Using the procedure of Example 1, (1R,trans)2,2-dimethyl-3-cyclopropylidenemethyl-cyclopropane-1-carboxylic acid was reacted to obtain (1-propargyl-2,4-dioxo-imidazolidin-3-yl)-methyl(1R,trans) 2,2-dimethyl-3-cyclopropylidenemethyl cyclopropane-1-carboxylate.
NMR Spectrum (deuterochloforom):

Peaks at 1.18–1.31 ppm (hydrogens of geminal methyls); at 1.09–1.10 ppm (hydrogens of —CH₂— of cycloproylidene); at 1.62–1.68 ppm (1-hydrogen of cyclopropyl); at 2.07–2.23–2.26–2.32 ppm (3-hydrogen of cyclopropane); at 2.37–2.40–2.43 ppm (acetylenic hydrogen); at 4.3 ppm (hydrogens of propargyl —CH₂—); at 4.1 ppm (5-hydrogens of imidazolidinyl ring); at 5.4–5.7 ppm (hydrogens of —CH₂— α to

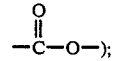

at 5.6 ppm (ethylenic hydrogen).

EXAMPLE 5

A soluble concentrate was prepared containing 0.25 g of the product of Example 2, 1 g of piperonyl butoxide, 0.25 g of Tween 80, 0.1 g of Topanol A and 98.4 g of water.

An emulsifiable concentrate was prepared containing 0.015 g of the product of Example 3, 0.5 g of piperonyl butoxide, 0.1 g of Topanol A, 95.885 g of xylene and 3.5 g of Tween 80.

A second emuslifiable concentrate was prepared containing 1.5 g of the product of Example 4, 20 g of Tween 80, 0.1 g of Topanol A and 78.4 g of xylene.

A fumigant composition was prepared containing 0.25 g of the product of Example 2, 25 g of tabu powder, 40 g of powdered cedar needles, 33.75 g of powdered pinewood, 0.5 g of brillant green and 0.5 g of nitrophenol.

INSECTICIDAL ACTIVITY

The knockdown effect of the products against housefiles was determined on 4 day old female houseflies by direct spraying at a concentration of 0.25 g/l in a Kearns and March chamber using as solvent a mixture of 5% acetone and 95% of Isopar L (petroleum solvent) and using 2 ml of solution per second. 50 insects were used for each test and the readings were taken every minute for 10 minutes and then at 15 minutes to determine the $KT_{50}$ values which are reported in Table I.

TABLE I

| Compound of Example | $KT_{50}$ in minutes |
| --- | --- |
| 1 | 2.3 |
| 2 | 0.6 |
| 3 | 0.61 |
| 4 | 0.58 |

The results of Table 1 show that the compounds of the invention possess a remarkable knockdown activity against houseflies.

Various modifications of the compounds and methods of the invention may be made without departing from the spirit or scope thereof and it should be understood that the invention is intended to be limited only as defined in the appended claims.

What we claim is:

1. An ester in all stereoisomeric forms or a mixture of said isomers of the formula

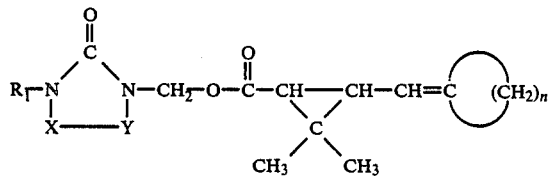

wherein one of X and Y is

and the other is selected from the group consisting of —CH$_2$—, —CH$_2$—CH$_2$— and —CH$_2$—CH$_2$—CH$_2$—, n is an integer from 2 to 3 and R$_1$ is selected from the group consisting of alkyl of 1 to 3 carbon atoms and alkenyl and alkynyl of 2 to 3 carbon atoms.

2. A compound of claim 1 wherein Y is

and X is —CH$_2$—.

3. A compound of claim 2 wherein R$_1$ is alkyl of 1 to 3 carbon atoms.

4. A compound of claim 2 wherein R$_1$ is alkenyl of 2 to 3 carbon atoms.

5. A compound of claim 2 wherein R$_1$ is alkynyl of 2 to 3 carbon atoms.

6. A compound of claim 2 wherein R$_1$ is —CH$_2$—C≡CH.

7. A compound of claim 1 selected from the group consisting of the (1-propargyl-2,4-dioxo-imidazolidin-3-yl)methyl ester of (1R,cis)2,2-dimethyl-3-cyclobutylidenemethyl-cyclopropane-1-carboxylic acid, (1R,trans)2,2-dimethyl-3-cyclobutylidenemethyl-cyclopropane-1-carboxylic acid, (1R,cis)2,2-dimethyl-3-cyclopropylidenemethyl-cyclopropane-1-carboxylic acid and (1R,trans)2,2-dimethyl-3-cyclopropylidenemethyl-cyclopropane-1-carboxylic acid.

8. An insecticidal composition comprising an insecticidally effective amount of at least one compound of claim 1 and an inert carrier.

9. A composition of claim 8 wherein Y is

and X is —CH$_2$—.

10. A composition of claim 9 wherein R$_1$ is alkyl of 1 to 3 carbon atoms.

11. A composition of claim 9 wherein R$_1$ is alkenyl of 2 to 3 carbon atoms.

12. A composition of claim 9 wherein R$_1$ is alkynyl of 2 to 3 carbon atoms.

13. A composition of claim 9 wherein R$_1$ is —CH$_2$—C≡CH.

14. A composition of claim 8 wherein the active ingredient is selected from the group consisting of (1-propargyl-2,4-dioxo-imidazolidin-3-yl)-methyl ester of (1R,cis)2,2-dimethyl-3-cyclobutylidenemethyl-cyclopropane-1-carboxylic acid, (1R,trans)2,2-dimethyl-3-cyclobutylidenemethyl-cyclopropane-1-carboxylic acid, (1R,cis)2,2-dimethyl-3-cyclopropylidenemethyl-cyclopropane-1-carboxylic acid and (1R,trans)2,2-dimethyl-3-cyclopropylidenemethyl-cyclopropane-1-carboxylic acid.

15. An acaricidal composition comprising an acaricidally effective amount of at least one compound of claim 1 and an inert carrier.

16. A nematocidal composition comprising a nematocidally effective amount of at least one compound of claim 1 and an inert carrier.

17. A composition for combatting parasites of warm-blooded animals comprising an amount of at least one compound effective to combat warm-blooded animals parasites and an inert carrier.

18. A method of combatting insects comprising contacting insects with an insecticidally effective amount of least one compound of claim 1.

19. A method of claim 18 wherein Y is

and X is —CH$_2$—.

20. A method of claim 19 wherein R$_1$ is alkyl of 1 to 3 carbon atoms.

21. A method of claim 19 wherein R$_1$ is alkenyl of 2 to 3 carbon atoms.

22. A method of claim 19 wherein $R_1$ is alkynyl of 2 to 3 carbon atoms.

23. A method of claim 19 wherein $R_1$ is —CH$_2$—C≡CH.

24. A method of claim 18 wherein the active ingredient is selected from the group consisting of (1-propargyl-2,4-dioxo-imidazolidin-3-yl)-methyl ester of (1R,cis)2,2-dimethyl-3-cyclobutylidenemethyl-cyclopropane-1-carboxylic acid, (1R,trans)2,2-dimethyl-3-cyclobutylidenemethyl-cyclopropane-1-carboxylic acid, (1R,cis)2,2-dimethyl-3-cyclopropylidenemethyl-cyclopropane-1-carboxylic acid and (1R,trans)2,2-dimethyl-3-cyclopropylidenemethyl-cyclopropane-1-carboxylic acid.

25. A method for combatting nematodes comprising applying to the soil a nematocidally effective amount of at least one compound of claim 1.

26. A method of combating acariens comprising contacting acariens with an acaricidally effective amount of at least one compound of claim 1.

27. A method of combatting parasites of warm-blooded animals comprising contacting the parasites with a pharmaceutically effective amount of at least one compound of claim 1.

28. An animal feed containing a pesticidally effective amount of at least one compound of claim 1.

* * * * *